United States Patent [19]

Cheng et al.

[11] 4,293,429

[45] Oct. 6, 1981

[54] MGO DISPENSIONS

[75] Inventors: William J. Cheng; David B. Guthrie; Donald M. Leiendecker, all of St. Louis, Mo.

[73] Assignee: Petrolite Corporation, St. Louis, Mo.

[21] Appl. No.: 112,495

[22] Filed: Jan. 16, 1980

[51] Int. Cl.³ .................. C10M 1/24; C10M 3/18; C10M 1/10; C10L 1/18
[52] U.S. Cl. ..................................... 252/18; 44/51; 44/DIG. 3; 252/25; 252/389 R
[58] Field of Search ............. 252/18, 25, 389 R; 44/51, DIG. 3

[56] References Cited

U.S. PATENT DOCUMENTS

| | | | |
|---|---|---|---|
| 2,616,904 | 11/1952 | Asseff et al. | 252/33 |
| 3,471,403 | 10/1969 | Le Suer et al. | 252/18 |
| 3,808,142 | 4/1974 | Crocker | 252/18 |
| 4,163,728 | 8/1979 | Cheng et al. | 252/18 |
| 4,179,383 | 12/1979 | Cheng et al. | 252/25 |

Primary Examiner—Delbert E. Gantz
Assistant Examiner—Irving Vaughn
Attorney, Agent, or Firm—Sidney B. Ring; Hyman F. Glass

[57] ABSTRACT

This invention relates to a stable, fluid magnesium oxide-containing dispersion prepared by the thermal treatment of MgO powder in a non-volatile fluid in the presence of a stoichiometric or lesser amount of a carboxylic acid as illustrated by acetic acid.

12 Claims, No Drawings

MGO DISPENSIONS

Heretofore, processes for obtaining dispersions of magnesium oxide which start with MgO powder do not result in products having long term stability in regard to suspensions of the solid particles. They are in actuality slurries of MgO powder.

In U.S. Pat. No. 4,163,728 there is described and claimed a process of preparing stable, fluid magnesium-containing dispersions and the preparation thereof by the high temperature decomposition of magnesium salts of carboxylic acids to sub-micron sized MgO in a dispersant-containing fluid, where less than a stoichiometric amount of carboxylic acid is employed in forming the magnesium carboxylates, based on Mg(OH)$_2$ or equivalent.

It is to be noted that the process of U.S. Pat. No. 4,163,728 to prepare stable, fluid dispersions of sub-micron sized MgO starts with Mg(OH)$_2$ and not MgO.

It is highly desirable to use MgO itself instead of Mg(OH)$_2$ in this type of process in view of the fact that MgO powder is significantly lower in cost than is Mg(OH)$_2$ powder since Mg(OH)$_2$, among other things, contains a molecule of H$_2$O per molecule of MgO. This fact not only increases the cost of equivalent MgO content but also increases the cost of shipping a molecule of water per molecule of MgO where this water is later dispelled.

We have now discovered that less expensive MgO can be employed as the starting material instead of Mg(OH)$_2$ as used in the process of U.S. Pat. No. 4,163,728 to form dispersions of sub-micron sized MgO.

Although the process of this invention has similarities to some extent to that employed in U.S. Pat. No. 4,163,728, an important exception is that MgO is employed as the starting material instead of Mg(OH)$_2$.

Other differences and advantages over U.S. Pat. No. 4,163,728 are:
  (1) the lower cost of MgO versus Mg(OH)$_2$
  (2) the operational temperature of the present process is lower (240°–310° C.) than the process of U.S. Pat. No. 4,163,728 (280°–330° C.).

Therefore, there is not only a savings in the cost of the starting material but also a saving in the energy requirements. These savings are important in these times of inflation and energy conservation.

The process of this invention which uses MgO powder can be carried out by employing stoichiometric or lesser amounts of carboxylic acid such as less than about 50%, for example 20–30%, or even 10% or less of the stoichiometric amounts of carboxylic acid. However, despite the fact that such minor stoichiometric amounts of carboxylic acids are employed, the yields of dispersed sub-micron sized MgO are substantially quantitative and are significantly greater than that achieved without such minor amounts of carboxylic acid.

Since a low stoichiometric amount of carboxylic acid is employed, the reactant is in essence a mixture of magnesium carboxylate and magnesium oxide.

Any suitable carboxylic acid at low stoichiometry can be employed. These include mono- and polycarboxylic acids including aliphatic, aromatic, cycloaliphatic, etc., carboxylic acids. Representative examples include: formic acid, maleic acid, etc. In view of the high volatility of aliphatic carboxylic acids, these are preferred, i.e., those of the formula

where R is aliphatic, preferably alkyl, such as those of the formula

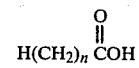

where n is about 0–9 such as about 0–5, but preferably 1.

The fluid dispersions of sub-micron sized MgO from magnesium carboxylate-magnesium oxide mixtures are achieved at a temperature range lower than for the dispersions of such MgO derived only from stoichiometric magnesium carboxylate such as magnesium carboxylate-magnesium oxide mixtures of the present invention is about 240°–310° C. This is about 20°–40° C. lower than the practical temperature range required for U.S. Pat. No. 4,163,728.

The conversion of Mg carboxylate—MgO mixture to dispersed sub-micron sized MgO is practically quantitative whereas the conversion of MgO in the absence of small amounts of magnesium carboxylate to effect the necessary dispersion is poor. Therefore in the practice of this invention, a portion of MgO is first transformed to magnesium carboxylate in situ in low stoichiometric amounts by the addition of carboxylic acid; and then the mixture of magnesium carboxylate—MgO is virtually quantitatively converted to dispersed sub-micron sized MgO at the process temperature in a dispersant-containing fluid.

Any suitable magnesium carboxylate capable of being subdivided upon decomposition into sub-micron particles of magnesia can be employed in the magnesium carboxylate-magnesium oxide mixture. Magnesium acetate is the preferred starting magnesium carboxylate compound in such mixture whether starting as the anhydrous solid, hydrated solid, aqueous slurry, aqueous solution, or as magnesium acetate formed in situ by the addition of acetic acid.

Any suitable non-volatile process fluid capable of being heated to the decomposition temperature of the magnesium carboxylate in the magnesium carboxylate-magnesium oxide mixture can be employed. The process fluid should be relatively stable and relatively non-volatile at the decomposition temperature. However, any volatility encountered is readily controlled by refluxing and condensing apparatus.

Examples of such non-volatile process fluids are as follows: hydrocarbons (such as mineral oil, paraffin oil, or aromatic oil), diphenyl oxide fluids, silicone oils, polyglycol ethers or vegetable oils, etc., solely the dispersant, or any combinations thereof.

The non-volatile process fluid should contain a dispersant(s) capable of retaining the sub-micron sized magnesium oxide in stable suspension. Any suitable dispersant which is relatively stable under the thermal conditions of this invention can be employed.

These are illustrated by the following: saturated and unsaturated fatty acids (such as stearic acid and oleic acid) and derivatives thereof (such as sorbitan monooleate), sulfonic acids (such as mahogany or petroleum derived sulfonic acids and synthetic sulfonic acids), naphthenic acids, oxyalkylated fatty amines, alkylphenols, sulfurized alkylphenols, oxyalkylated alkylphenols, etc.

The reaction is carried out as follows. Although the decomposition temperature of magnesium acetate to magnesium oxide is about 323° C. (613° F.), the reactant mixture of this invention containing both magnesium acetate and magnesium oxide is heated above 230° C. The volatile products from such mixtures are removed from the reaction. In practice, temperatures of about 230° C. to 330° C. are employed, such as from about 235° C. to 320° C., but preferably from about 240° C. to 310° C.

The particle size of the resulting MgO so formed in general is of a size which is stable and fluid. In practice, the particle size is no greater than about 5 microns, such as no greater than about 2 microns, but preferably no greater than about one micron.

The concentration of the magnesium oxide so formed in the non-volatile process fluid should be no greater than that concentration which maintains suitable fluidity. In general, the final concentration based on non-volatile fluid and other materials is from about 1% to 32% when calculated as percent magnesium, such as from about 2% to 29%, for example, from about 3% to 26%, but preferably from about 4% to 23%.

The concentration of the dispersant in the non-volatile process fluid should be sufficient to maintain a fluid, stable dispersion of sub-micron sized magnesium oxide in the fluid. In general the weight concentration of dispersant and non-volatile fluid may range from 100% dispersant and 0% non-volatile fluid to as little as 0.01% dispersant and 99.99% fluid, such as from about 95% and 5%, for example from about 90% to 10%, but preferably from about 85 to 15%.

In the actual practice of commercializing the conversion of magnesium oxide to a stable fluid dispersion of sub-micron sized MgO, we believe that the coarse particles in magnesium oxide are disintegrated by the action of small amounts of magnesium acetate prior to the dispersion-forming step, from which state the magnesium acetate-magnesium oxide mixture is readily converted quantitatively by the appropriate thermal treatment into a stable fluid dispersion of sub-micron sized MgO.

In accord with the present invention, dispersions of magnesium oxide are now prepared from magnesium oxide by utilizing the principle of forming magnesium acetate in situ by employing low stoichiometry of acetic acid based on MgO, from which state the starting magnesium oxide is converted quantitatively into dispersible, sub-micron sized magnesium oxide which can be marketed as a stable dispersion rather than an unstable slurry of MgO powder.

The stable dispersions of sub-micron sized MgO of this invention can be further reacted to form dispersions of the corresponding derivatives. For example, after formation in accord with this invention, the MgO dispersions can be further reacted with $CO_2$ to form $MgCO_3$ dispersions, reacted with $H_2O$ to form $Mg(OH)_2$ dispersions, etc.

The compositions of this invention have a wide variety of uses. The following are illustrative:
1. As a combination anti-corrosion and acidic neutralization additive for lubricating oils and greases.
2. As a combination anti-corrosion and acidic neutralization additive during the combustion of fuels such as residual fuel, pulverized sulfur-containing coal, or mixtures thereof.
3. As a combination anti-weathering and sealing agent for water-proofing cement, concrete, and asphaltic surfaces.
4. In proprietary pharmaceutical and cosmetic formulations.
5. As corrosion inhibitors, particularly in fuels containing vanadium.

USE AS CORROSION INHIBITOR FOR VANADIUM-CONTAINING FUELS

The demand for greatly increased amounts of energy has forced utilities and other large-quantity users of fossil fuels to explore low-quality fuels for use in steam boilers and gas turbines. Fuels such as unrefined crude oil and residual oil contain large amounts of impurities which result in corrosive deposits in the equipment. Two of these impurities, sodium and vanadium, form catastrophically corrosive, low melting slags that can destroy a vital part in a matter of hours.

Crude oil usually contains 1–500 ppm of vanadium in the form of a porphyrin complex depending on the source. Because of its origin as a concentrate from the refining process, residual oil contains several times more vanadium than the crude from which it was derived. The combustion of these vanadium-containing fuels produces very corrosive $V_2O_5$ deposits which can destroy a turbine part in a matter of hours. Although the vanadium can be removed, the cost of the process cancels the economic advantage of using unrefined fuels. Vanadic corrosion is, therefore, usually controlled with chemical additives and optimization of operating conditions.

Sodium is almost always present in low-quality fuels, either directly in the crude oil or indirectly through contamination from various sources. The technology for removing sodium is well developed. These are limiting processes, however, and a trace of sodium must always be dealt with. For example, in maritime use the sodium level can be increased because of the introduction of sodium chloride through the air intake and contamination of the fuel by sea water. During combustion, the sodium reacts with the sulfur in the fuel to form the sulfate which is deposited in turbine parts. This reaction has been shown to be thermodynamically favored and results in the only sodium compound that will deposit under these conditions.

The mechanism of corrosion by vanadium and sodium has received much attention. Nascent oxygen species has been proposed as the corrosive active agent in $V_2O_5$ melts. Various mechanisms have been presented to explain corrosive attack by sodium sulfate at metal surfaces. The classical method of inhibiting the corrosive characteristics of $V_2O_5$ and $Na_2SO_4$ melts has been to form high-melting vanadates of the former and minimize the level of the latter. Magnesium has been the most successful substance for this type of protection. The optimum levels of magnesium addition are not precisely known. Just as the mechanism of corrosion is only partially understood, so too is that of its inhibition.

There are other methods of limiting the corrosion such as reducing the operating temperature and maintaining the air to fuel ratio so that slightly reducing conditions exist during combustion. These types of methods may not be applicable. For example, the air to fuel ratio cannot be lowered to obtain reducing conditions in a gas turbine. Lower operating temperatures make the system less efficient and may be ruled out for economic reasons. Thus, chemical additives are often the best way to inhibit corrosion.

The compositions of this invention inhibit fireside corrosion in gas turbines, steam boilers and furnaces when incorporated into petroleum fuels in minor but effective amounts such as from about 1 to 2000 ppm, for example from 1 to 1000 ppm, but preferably from about 1 to 100 ppm, based on magnesium content.

USE AS ADDITIVES FOR AUTOMOTIVE AND INDUSTRIAL LUBRICANTS

A chemical additive in the usual sense refers to a material which enhances a desirable property while eliminating or minimizing one or more undesirable ones. Since about 1930 the commercial application of chemical additives to lubricating oils has kept pace with the increasing demands of modern machinery, such as automotive engines, high-speed machinery, high-pressure hydraulic control systems, etc. The literature and patent art are replete with examples of such additives which in general improve the lubrication performance for the machinery while minimizing the frequency of maintenance.

For combating the severe rust conditions which may be encountered during shipping of machinery or in long storage or exposure to out-door weather, sodium and calcium sulfonate additives are commonly used.

Additives for imparting detergency to lubricating oils are widely used at 2–20% concentration and are found to prevent or remove deposits of oil-insoluable sludge, varnish, carbon and lead compounds which otherwise form on internal combustion engine parts. The additives probably act by absorbing and suspending the insoluble particles so that deposits are minimized, and cleanliness of rings, valves, and cylinder walls are maintained. Commercial detergent additive for such automotive and diesel engine oils are designed also to react chemically with the highly acidic by-products of combustion that find their way into the lubricating oil system. The additives with this type of functionality are usually comprised of basic barium, calcium, and magnesium salts of oil-soluble organic compounds.

A discussion of the preparation and use of overbased or hyperbasic detergent sulfonates is found in U.S. Pat. No. 3,057,896. The term "metal ratio," as used to describe the amount of overbasing or hyperbasic detergency in the additive, is defined as the ratio of equivalents of metal to equivalents of organic acid. The important metals which readily provide such overbasing are those of the alkaline earth group, particularly magnesium, calcium, and barium.

The products of this invention at a metal ratio of about 15–16/1 can be employed as hyperbasic additives for lubricating oils.

Except for Ser. No. 816,626 and U.S. Pat. Nos. 4,163,728 and 4,179,383, prior art procedures do not prepare MgO dispersions by employing the high temperature range which is necessary for the product and process of this invention, and therefore, do not achieve a stable dispersible sub-micron sized magnesium oxide but instead attempt to achieve magnesium oxide suspensions.

In our invention the preferable dispersing agent is an organic carboxylic acid or sulfonic acid or any mixture thereof which reacts with a magnesium compound to form a salt or other complex. The magnesium salt or complex of such acid moiety is formed by the reaction of an equivalent of basic magnesium moiety (such as, for example, magnesium oxide, magnesium hydroxide, magnesium carbonate, or any mixtures thereof) with a corresponding equivalent of acid moiety.

The following examples are presented for purposes of illustration and not of limitation.

EXAMPLE 1

Example 1 describes a preparation of an oil dispersion of sub-micron sized MgO when the starting magnesium oxide is a reagent grade material A low stoichiometric amount of acetic acid is used to make magnesium acetate in situ. The amount of water added was calculated to be the amount necessary to make $Mg(OAc)_2.4H_2O$; although it is possible that the $H_2O$ added can also react with MgO to form $Mg(OH)_2$, nevertheless the water added is readily removed by the thermal conditions of the process of this invention.

To a one-gallon S.S pressure reactor having agitator and thermometer was charged a mixture containing 675 g process oil, 227 g naphthenic acid, and 257 g reagent grade magnesium oxide; 33 g $H_2O$ and 74 g glacial acetic acid followed. The contents were heated to 147° C. and 12 psig and maintained at that temperature for three hours. A 636.8 gram aliquot of the above mixture was heated in a one-liter 3-necked glass reactor having agitator, thermometer, and Dean/Stark assembly for distillation to remove water with a return of process oil which co-distills. The contents of the reactor were heated to 287° C. to distill off all the water that would evolve while returning any oil which co-distilled. The material was clear and bright. The mass was heated to 315° C. with a trace of additional water being removed. The product was calculated to contain 16.2% as Mg. The product upon centrifugation for 2 hours gave virtually no sediment.

EXAMPLE 2

The importance of low stoichiometric amounts of acetic acid in Example 1 is demonstrated by this Example 2. The procedure of Example 1 was the same except that no acetic acid was used. The resulting product was not clear and bright; upon centrifugation more than 20% separation of solids was indicated.

EXAMPLE 3

Example 3 describes a 10-gallon preparation according to the procedure of Example 1 except that the entire process was carried out in a single reactor. The starting magnesium oxide was a commercial source of technical grade material.

To a 10-gallon pressure reactor were charged: hydrocarbon solvent, 33⅛lbs; naphthenic acid, 15⅜lbs; magnesium oxide (commercial, tech grade), 15⅞lbs; acetic acid 4½lbs; and $H_2O$, 7¼lbs. The contents of the reactor were heated under pressure at a temperature of 200°–235° C. for 15 hours. The reactor pressure was vented and the contents heated further to effect distillation of any water, etc. Upon reaching 304° C., there was no further water distilling. The product was clear and bright. The magnesium content was calculated at 19.5%, and the sediment obtained was 0.95% after centrifugation for five hours; the bulk of the sediment separated quickly.

The above illustrates the invention. Obvious modifications are evident to those skilled in the art. For example, stoichiometric amounts of carboxylic acid can be employed, if desired. However, there is no commercial advantage in so doing.

We claim:

1. A process of preparing a stable, fluid magnesium oxide containing dispersion which comprises heating MgO powder at a temperature greater than 230° C. in a relatively stable, relatively non-volatile process fluid capable of being heated to a temperature greater than about 230° C. in the presence of less than a stoichiometric amount of carboxylic acid, based on MgO. whereby the carboxylate is formed in situ and decomposes to form said MgO.

2. The process of claim 1 where the decomposition temperature is about 230° C. to about 330° C.

3. The process of claim 2 where the carboxylic acid is acetic acid.

4. The process of claim 1 where the process contains less than about 50% stoichiometric amount of carboxylic acid.

5. The process of claim 2 where the process contains less than about 50% stoichiometric amount of carboxylic acid.

6. The process of claim 3 where the process contains less than about 50% stoichiometric amount of carboxylic acid.

7. The process of claim 4 where the process contains less than about 20% stoichiometric amount of carboxylic acid.

8. The process of claim 5 where the process contains less than about 20% stoichiometric amount of carboxylic acid.

9. The process of claim 6 where the process contains less than about 20% stoichiometric amount of carboxylic acid.

10. The process of claim 1 where the particle size of the MgO formed is no greater than about 5 microns.

11. The process of claim 1 where the particle size of the MgO formed is no greater than about 2 microns.

12. The process of claim 1 where the particle size of the MgO formed is no greater than about 1 micron.

* * * * *

UNITED STATES PATENT AND TRADEMARK OFFICE
CERTIFICATE OF CORRECTION

PATENT NO. : 4,293,429
DATED : October 6, 1981
INVENTOR(S) : William J. Cheng, David B. Guthrie and Donald M. Leiendecker It is certified that error appears in the above—identified patent and that said Letters Patent is hereby corrected as shown below:

On the title, "MGO" should read

--- MgO ---

Signed and Sealed this

Twenty-fourth Day of August 1982

|SEAL|

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,293,429

DATED : October 6, 1981

INVENTOR(S) : William J. Cheng, David B. Guthrie, and Donald M. Leiendecker

It is certified that error appears in the above—identified patent and that said Letters Patent is hereby corrected as shown below:

On the title page

In the title, "MGO Dispensions" should read

--- MgO Dispersions ---

Signed and Sealed this

*Twenty-first* Day of *September 1982*

[SEAL]

Attest:

Attesting Officer

GERALD J. MOSSINGHOFF

*Commissioner of Patents and Trademarks*